(12) United States Patent
Loveday et al.

(10) Patent No.: US 10,544,158 B1
(45) Date of Patent: Jan. 28, 2020

(54) PROCESS FOR PRODUCING POLYCYCLIC POLYETHER POLYOLS

(71) Applicant: COVESTRO LLC, Pittsburgh, PA (US)

(72) Inventors: Anthony R. Loveday, Weirton, WV (US); Jack R. Reese, Coraopolis, PA (US); Rick L. Adkins, Canonsburg, PA (US); David P. Zielinski, Cranberry Township, PA (US)

(73) Assignee: Covestro LLC, Pittsburgh, PA (US)

( * ) Notice: Subject to any disclaimer, the term of this patent is extended or adjusted under 35 U.S.C. 154(b) by 0 days.

(21) Appl. No.: 16/373,885

(22) Filed: Apr. 3, 2019

Related U.S. Application Data

(60) Provisional application No. 62/818,228, filed on Mar. 14, 2019.

(51) Int. Cl.
   *C07D 493/04* (2006.01)
   *C07C 41/03* (2006.01)
   *B01J 27/26* (2006.01)
   *C08G 18/48* (2006.01)

(52) U.S. Cl.
   CPC .......... *C07D 493/04* (2013.01); *C07C 41/03* (2013.01); *B01J 27/26* (2013.01); *C07C 2602/42* (2017.05); *C07C 2602/44* (2017.05); *C07C 2602/46* (2017.05); *C07C 2602/48* (2017.05); *C07C 2603/66* (2017.05); *C08G 18/4875* (2013.01); *C08G 18/4883* (2013.01)

(58) Field of Classification Search
   CPC ... C07D 493/04; C07C 41/03; C07C 2602/44; C07C 2602/48; C07C 2602/42; C07C 2603/66; C07C 2602/46; C08G 18/4883; C08G 18/4875; B01J 27/26
   See application file for complete search history.

(56) References Cited

U.S. PATENT DOCUMENTS

| | | | |
|---|---|---|---|
| 5,847,069 A * | 12/1998 | Greco | C08G 18/44 528/196 |
| 7,887,982 B2 | 2/2011 | Vijayendran et al. | |
| 8,053,468 B2 | 11/2011 | Selifonov | |
| 8,367,171 B2 | 2/2013 | Stenson et al. | |
| 8,420,747 B2 | 4/2013 | Malinoski et al. | |
| 8,895,660 B2 | 11/2014 | Alidedeoglu et al. | |
| 9,109,137 B2 | 8/2015 | Lindekens et al. | |
| 9,475,956 B2 | 10/2016 | Beccaria et al. | |
| 2009/0018300 A1 | 1/2009 | Bloom et al. | |
| 2009/0226644 A1 | 9/2009 | Wylie et al. | |
| 2013/0261222 A1 | 10/2013 | Schiraldi et al. | |
| 2017/0291989 A1 | 10/2017 | Delmas et al. | |
| 2018/0016385 A1 | 1/2018 | Ryu et al. | |

FOREIGN PATENT DOCUMENTS

| | | |
|---|---|---|
| WO | 2012005648 A1 | 1/2012 |
| WO | 2017003620 A1 | 1/2017 |

OTHER PUBLICATIONS

Jiang et al; "Synthesis and characterization of polyurethane rigid foams from polyether polyols with isosorbide as the bio-based starting agent"; Journal of Polymer Research (2018) 25: 140; Published online: May 22, 2018; Springer Science+Business Media B.V., part of Springer Nature 2018.

* cited by examiner

*Primary Examiner* — John M Mauro
(74) *Attorney, Agent, or Firm* — Donald R. Palladino

(57) ABSTRACT

Processes are described for producing a polycyclic polyether polyol having a hydroxyl functionality of 1.5 to 6 and a number average molecular weight of 200 to 12,000 Da. The processes comprise alkoxylating a polyol starter comprising predominantly a polycyclic polyol with an alkylene oxide in the presence of a DMC catalyst.

21 Claims, No Drawings

PROCESS FOR PRODUCING POLYCYCLIC POLYETHER POLYOLS

FIELD

The present invention relates to the production of polycyclic polyether polyols using double metal cyanide ("DMC") catalysts.

BACKGROUND

Polyether polyols are used in a wide variety of applications and are often prepared by reaction of a suitable starter (or initiator) compound with one or more alkylene oxides in the presence of one or more catalysts. Often, the starter or initiator includes a compound having two or more hydroxyl groups per molecule (i.e. diols, triols, and other higher polyols). Polyether polyols of this type are well known in the field of polyurethane chemistry.

One area of interest for the use of polyurethanes is as a gel coat in the construction of glass fiber reinforced plastics ("FRPs"), such as those used in the construction of marine craft, showers and bathtubs, building and automotive panels, swimming pools, and satellite dishes. In conventional FRP construction, a release agent, such as a wax, is applied to a mold, a gel coat is applied to the waxed mold, and a glass fiber reinforced laminate is applied to the gel coat. The FRP is ultimately removed from the mold to provide the glass fiber reinforced laminate covered by a decorative gel coat layer. The gel coat layer should provide a desired hardness, aesthetic appearance, durability, ultraviolet degradation resistance and hydrolysis resistance to the FRP. In addition, the gel coat should adhere well to an unsaturated polyester backing resin. Finally, the use of renewable resources for the production of such gel coats is sought from an environmental sustainability perspective.

As a result, it would be desirable to provide a method for producing polyether polyols using a renewable starter that can be used in the production of polyurethane coatings, particularly polyurethane gel coatings.

SUMMARY

In certain respects, the specification relates to a process for producing a polycyclic polyether polyol having a hydroxyl functionality of 1.5 to 6 and a number average molecular weight of 200 to 12,000 Da. The method comprises alkoxylating a polyol starter comprising predominantly a polycyclic polyol with an alkylene oxide in the presence of a DMC catalyst.

In other respects, the specification relates to a process for producing a polycyclic polyether polyol having a hydroxyl functionality of 1.5 to 3 and a number average molecular weight of 200 to 800 Da. The method comprises alkoxylating a polyol starter consisting essentially of a 1,4:3,6-dianhydrohexitol having a purity of greater than 98%, with an alkylene oxide in the presence of a DMC catalyst.

DETAILED DESCRIPTION

Various embodiments are described and illustrated in this specification to provide an overall understanding of the structure, function, properties, and use of the disclosed inventions. It is understood that the various embodiments described and illustrated in this specification are non-limiting and non-exhaustive. Thus, the invention is not limited by the description of the various non-limiting and non-exhaustive embodiments disclosed in this specification. The features and characteristics described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant(s) reserve the right to amend the claims to affirmatively disclaim features or characteristics that may be present in the prior art. Therefore, any such amendments comply with the requirements of 35 U.S.C. § 112 and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant(s) reserves the right to amend this specification to expressly recite any subject matter, or portion thereof, incorporated by reference herein.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant(s) reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112 and 35 U.S.C. § 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

As used herein, the term "functionality" refers to the average number of reactive hydroxyl groups, —OH, present per molecule of a polyol or polyol blend that is being described. As used in this specification, the "arithmetically calculated functionality" of a polyol is based on resin solids and is calculated by adding reacted water with the hydroxyl equivalents of the reacted other polyhydroxyl compound(s), such as sucrose, divided by the hydroxyl equivalents of the reacted water multiplied by its functionality (2) plus the hydroxyl equivalents of the reacted other polyhydroxyl compound(s) sucrose multiplied by their functionality, such as (8) in the case of sucrose. The amount of reacted water is calculated by analyzing, using gas chromatography, the weight percent of glycol in the resultant polyol.

As used herein, the term "hydroxyl number" refers to the number of reactive hydroxyl groups available for reaction, and is expressed as the number of milligrams of potassium hydroxide equivalent to the hydroxyl content of one gram of the polyol, and is determined according to ASTM D4274-16. The term "equivalent weight" refers to the weight of a compound divided by its valence. For a polyol, the equivalent weight is the weight of the polyol that will combine with an isocyanate group, and may be calculated by dividing the molecular weight of the polyol by its functionality. The equivalent weight of a polyol may also be calculated by dividing 56,100 by the hydroxyl number of the polyol—Equivalent Weight (g/eq)=(56.1×1000)/OH number.

The viscosity values of a polyol reported herein, if any, refer to a viscosity determined using an Anton-Paar SVM 3000 viscometer at 25° C. that has been demonstrated to give equivalent results as can be generated with ASTM-D4878-15, in which the instrument has been calibrated using mineral oil reference standards of known viscosity.

The number average and weight average, Mn and Mw, respectively, molecular weights reported herein can be determined by gel-permeation chromatography (GPC) using a method based on DIN 55672-1, employing chloroform as the eluent with a mixed bed column (Agilent PL Gel; SDVB; 3 micron Pore diameter: 1× Mixed-E+5 micron Pore diameter: 2× Mixed-D), refractive index (RI) detection and calibrated with polyethylene glycol as the standard.

As indicated, certain embodiments of the present specification are directed to processes for producing a polycyclic polyether polyol. The polycyclic polyether polyols produced according to the processes of this specification can have an arithmetically calculated functionality of, for example, at least 1.5, such as 1.5 to 6, 1.5 to 4, 1.5 to 3, 2 to 3, or 2 to 2.5. In certain implementations, the polycyclic polyether polyol has a number average molecular weight of 200 Da to 12,000 Da, such as 200 Da to 1,500 Da, 200 Da to 1,000 Da, 200 Da to 800 Da, 200 Da to 600 Da, 200 Da to 400 Da, or 250 Da to 350 Da. In some embodiments, the polycyclic polyether polyols produced according to the processes of the present specification have a viscosity at 25° C. of no more than 7500 cks, such as no more 5000 cks, no more than 1500 cks, no more than 1000 cks, such as 300 cks to 1,500 cks. In some embodiments, the polyether polyols produced according to the processes of this specification exhibit an APHA (Pt/Co) color (ASTM D1209-05) of no more than 500, such as no more than 400, no more than 300, no more than 200, in some cases, no more than 150 or no more than 100.

The processes of this specification comprise alkoxylating a polyol starter comprising predominantly a polycyclic polyol with an alkylene oxide in the presence of a DMC catalyst. As used herein, when it is stated that a polyol starter comprises "predominantly" a polycyclic polyol, it means that the polycyclic polyol starter is used in an amount of greater than 50% by weight, based on the total weight of polyol starter used to produce the polycyclic polyether polyol.

As used herein, the term "polycyclic polyol" refers to a compound that includes, per molecule, at least two reactive —OH groups and at least two cyclic groups in which one or more atoms (sometimes two or more atoms) are present in the rings of at least two cyclic groups. A polycyclic polyol starter can be monomeric or it can polymeric, such as would be the case where the polycyclic polyol starter is any type of polycyclic polyether polyol produced as described in this specification. In some implementations, the polycyclic polyol starter comprises a polycyclic diol, i.e., a polycyclic polyol that contains two reactive —OH groups per molecule. Polycyclic triols (three reactive —OH groups per molecule) and higher functionality polyols can, however, also be readily envisioned.

In some implementations, the polycyclic polyol starter comprises a bicyclic polyol (two rings per molecule), a tricyclic polyol (three rings per molecule), and/or a polycyclic polyol that includes four or more rings per molecule. In each case, the rings of the polycyclic group may be saturated, i.e., aliphatic, or unsaturated. Moreover, in each case, the polycyclic groups may include any combination of cyclic groups of various ring sizes, including rings of 3 atoms, 4 atoms, 5 atoms, 6 atoms, and/or 7 or more atoms. Furthermore, in each case, the polycyclic groups may be unsubstituted or substituted, such as with one or more heteroatoms, such as nitrogen, oxygen, silicon, sulfur and/or another heteroatom. In certain implementations, the polycyclic polyol starter comprises a dicyclic diol in which the cyclic groups include an ether (C—O—C) linkage.

In some implementations, the polycyclic polyol starter comprises a bicyclic diol and/or a tricyclic diol. Specific examples of suitable bicyclic and tricyclic units that may be present in such bicyclic diols and tricyclic diols are tricyclodecane (structure A), bicyclodecane (structure B), norbornane (structure C), bicyclooctane (structure D), bicyclononane (structure E), isosorbide (structure F), and bicycloundecane:

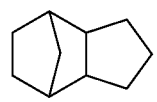

A

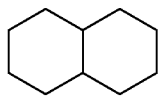

B

C

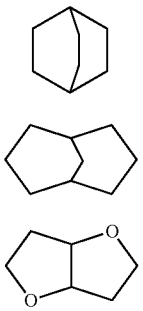

In some implementations, the polycyclic polyol starter comprises a dicyclic diol comprising any of the 1,4:3,6-dianhydrohexitols, such as isosorbide, isomannide, isoidide, isogalactide, isofucide and isoinoside.

Furthermore, it was discovered, surprisingly, that the ability to alkoxylate a 1,4:3,6-dianhydrohexitol in the presence of a DMC catalyst varied significantly with seemingly very small changes in the purity of the 1,4:3,6-dianhydrohexitol that is employed as the starter. In particular, it was discovered that, particularly when producing a polycyclic polyether polyol having a hydroxyl functionality of 1.5 to 3 and a number average molecular weight of 200 to 800 Da using a 1,4:3,6-dianhydrohexitol as essentially the entire H-functional starter (at least 90% by weight based on the total weight of H-functional starter) it was important to utilize a 1,4:3,6-dianhydrohexitol having a purity of greater than 98%, such as at least 98.5%, at least 99%, or, in some cases, greater than 99.5%, and to use a DMC catalyst in an amount of at least 0.01% by weight, such as at least 0.02% by weight, based on the total weight the polycyclic polyether polyol, in order to effectively alkoxylate the 1,4:3,6-dianhydrohexitol to produce a polycyclic polyether polyol at all, even more particularly one having an APHA (Pt/Co) color of less than 200.

As a result, in certain implementations, this specification is directed to a process for producing a polycyclic polyether polyol having a hydroxyl functionality of 1.5 to 3 and a number average molecular weight of 200 to 800 Da. The method comprises alkoxylating a polyol starter consisting essentially of a 1,4:3,6-dianhydrohexitol having a purity of greater than 98%, such as at least 99%, with an alkylene oxide in the presence of a DMC catalyst, wherein the DMC catalyst is used in an amount of at least 0.01% by weight, such as at least 0.02% by weight, based on the total weight of the polycyclic polyether polyol.

If desired, in addition to the polycyclic polyol starter, other H-functional starters, including other polyol starters, may be used. In some implementations, one or more additional hydroxyl and/or amine functional starters is employed. In some implementations, for example, such additional starter(s) may comprise trimethylolethane, trimethylolpropane, glycerol, pentaerythritol, 4,4'-dihydroxydiphenyl-propane, sorbitol, sucrose, ethylenediamine, monoethanolamine, diethanolamine, methyl amine, ethylene diamine, diethylene triamine, triethylene tetramine, triethanolamine, ethylene glycol, 1,2- or 1,3-propanediol, 1,2-, 1,3- or 1,4-butanediol, 1,5-heptanediol, 1,6-hexanediol, 1,4-cyclohexanedimethanol, 1,4-cyclohexanedimethanol, 1,3-cyclohexanedimethanol, 1,2-cyclohexanedimethanol, tricyclodecanedimethanol, adamantanediol, pentacyclopentadecanedimethanol, glycerin, pentaerythritol, 4,4'-dihydroxy-diphenylpropane, aniline, 4,4'-methylene dianiline, 2,3-toluene diamine, 3,4-toluene diamine, 2,4-toluene diamine, and 2,6-toluene diamine, ammonia, ethanolamine, triethanolamine, and ethylene diamine, or a mixture of any two or more of the foregoing. Oligomeric and/or polymeric polyols, such as polyether polyols, including polycyclic polyether polyols, are also suitable starters, as are methylene-bridged polyphenyl polyamines composed of isomers of methylene dianilines and triamines or polyamines of higher molecular weight prepared by reacting aniline with formaldehyde, and Mannich reaction products of phenol or substituted phenols with alkanol amines and formaldehyde or paraformaldehyde.

In some implementations, however, the polycyclic polyol starter is present in an amount of more than 50% by weight, in some cases, at least 80% by weight, at least 90% by weight, or, in yet other cases, at least 98% by weight or at least 99% by weight, based on the total weight of H-functional initiator used to prepare the polycyclic polyether polyol.

As indicated earlier, the processes of this specification comprise alkoxylating the polyol starter with an alkylene oxide. Suitable alkylene oxides include, for example, ethylene oxide, propylene oxide, butylene oxide, styrene oxide, epichlorohydrin, as well as mixtures of any two or more thereof. If more than one type of alkylene oxide, is used, they can be used sequentially or simultaneously.

In the processes of this specification, the alkoxylation is conducting in the presence of a DMC catalyst. Suitable DMC catalysts include both crystalline catalysts and non-crystalline (i.e. substantially amorphous) catalysts. Crystalline DMC catalysts are known and described in, for example, U.S. Pat. Nos. 6,303,833 and 6,303,533, the disclosures of which being incorporated herein by reference.

In some implementations, the DMC catalyst that is employed exhibits a substantially non-crystalline character (substantially amorphous) such as is disclosed in U.S. Pat. Nos. 5,482,908 and 5,783,513, the disclosures of which being incorporated herein by reference.

Specific examples of double metal cyanide compounds that can be used in the processes of this specification include, for example, zinc hexacyanocobaltate(II), zinc hexacyano-ferrate(III), nickel hexacyanoferrate(II), cobalt hexacyano-cobaltate(III), and the like. Further examples of suitable double metal cyanide complexes are listed in U.S. Pat. No. 5,158,922, the disclosure of which is incorporated herein by reference.

Solid DMC catalysts suitable for use in the processes of this specification include an organic complexing agent. Generally, the complexing agent must be relatively soluble in water. Suitable complexing agents are disclosed, for example, in the aforementioned U.S. Pat. No. 5,158,922. The complexing agent may be added either during preparation or immediately following precipitation of the catalyst. Usually, an excess amount of the complexing agent is used. In some implementations, the complexing agent comprises a water-soluble heteroatom-containing organic compound that can complex with the double metal cyanide compound. Specific examples of suitable complexing agents include, but are not limited to, alcohols, aldehydes, ketones, ethers, esters, amides, ureas, nitriles, sulfides, and mixtures thereof. In some cases, the complexing agent comprises a water-soluble aliphatic alcohol selected from the group consisting of ethanol, isopropyl alcohol, n-butyl alcohol, isobutyl alcohol, sec-butyl alcohol, and tert-butyl alcohol.

In some implementations, the solid DMC catalyst includes from 5 to 80% by weight, such as 10 to 70% by weight or, in some cases 15 to 60% by weight, based on the total catalyst weight, of a polyether having a number average molecular weight greater than 500. Suitable polyethers include those produced by ring-opening polymerization of cyclic ethers, and include epoxide polymers, oxetane polymers, tetrahydrofuran polymers, and the like. Any method of catalysis can be used to make the polyethers. The polyethers can have any desired end groups, including, for example, hydroxyl, amine, ester, ether, or the like. In some cases, the polyether comprises a polyether polyol having average hydroxyl functionalities from 2 to 8 and number average molecular weights within the range of 1000 to 10,000, such as 1000 to 5000. These are often made by polymerizing epoxides in the presence of active hydrogen-containing initiators and basic, acidic, or organometallic catalysts (including DMC catalysts). Useful polyether polyols include poly(oxypropylene) polyols, EO-capped poly(oxypropylene) polyols, mixed EO-PO polyols, butylene oxide polymers, butylene oxide copolymers with ethylene oxide and/or propylene oxide, polytetramethylene ether glycols, and the like. In some implementations, the poly(oxypropylene) polyol may be specifically diols and/or triols having number average molecular weights within the range of 2000 to 4000.

The DMC catalyst concentration in the inventive process is chosen to ensure a good control of the polyoxyalkylation reaction under the given reaction conditions. The catalyst concentration is at least 0.001 wt. % or higher, at least about 0.0024 wt. % or higher, or at least about 0.0025 wt. % or higher. The catalyst concentration is also typically less than or equal to about 0.2 wt. %, or less than or equal to about 0.1 wt. %, or less than or equal to about 0.06 wt. %. Thus, the catalyst concentration may range from about 0.001 wt. % to about 0.2 wt. %, or in the range from about 0.0024 wt. % to about 0.1 wt. %, or in the range of from about 0.0025 to about 0.06 wt. %, based on the weight of the polyol produced. The substantially non-crystalline DMC catalyst may be present in an amount ranging between any combination of these values, inclusive of the recited values.

In certain implementations of the process of this specification, the polycyclic polyol starter (and possibly other starters) and DMC catalyst are charged to the reactor and stripped for about 30 minutes at a temperature in the range of 100° C. to 150° C. with or without a nitrogen sparge. The polycyclic polyol starter, if a solid, may be melted prior to being charged to the reactor or it may be charged to the reactor as a solid. Vacuum is optional but may be used if desired. The reactor contents are heated (usually at a temperature of 100° C. to 150° C.), and oxide is added to activate the catalyst. A decrease in reactor pressure is an indication that the DMC catalyst is activated. After activation of the DMC catalyst, the remaining oxide is fed to the reactor, often at a temperature of 130° C. to 170° C. Residual oxide can be digested after the oxide feed for approximately 30 minutes to 60 minutes. Vacuum stripping is optional but if done, it is typically for between 20 and 30 minutes.

In some implementations, the polycyclic polyol starter can be continuously dosed into the reaction mixture during the alkoxylation once the reaction has initiated. This can be accomplished by, for example, melting the polycyclic polyol in a vessel separate from the reactor and dosing the polycyclic polyol into the reaction mixture through heated lines, electrically heat traced or by other mechanisms, using a suitable pumping mechanism or by pressure feeding at a controlled rate.

The polyether polyols produced by the process described in this specification can be used in a variety of applications. In some cases, however, they are useful for producing rigid polyurethane foams or in the production of polyurethane coatings. Such foams and coatings can be produced by reacting an organic polyisocyanate with a polyether polyol produced by the processes of this specification at an isocyanate index of from 0.9 to 3.1, such as 1.05 to 1.55. In the case of foams, this reaction is conducted in the presence of a blowing agent.

In the case of coatings, the polyisocyanate that is used is often a non-aromatic polyisocyanate. Non-limiting examples of suitable non-aromatic polyisocyanates include monomeric aliphatic, cycloaliphatic, and/or araliphatic diisocyanates. Examples of diisocyanates include 1,6-diisocyanatohexane, 1-isocyanato-3,3,5-tri-methyl-5-isocyanatomethylcyclohexane (isophorone diisocyanate), 4,4-diisocyanatodicyclohexylmethane, 1,4-diisocyanatocyclohexane, 1-methyl-2,4-diisocyanatocyclohexane, 1-methyl-2,6-diisocyanatocyclohexane and mixtures thereof.

The polyisocyanates of the aforementioned kind often have an NCO group content of 10 to 25% by weight, an average NCO functionality of 2.0 to 5.0, and a residual amount of monomeric diisocyanates, used for their preparation, of below 1% by weight, often below 0.5% by weight.

Suitable polyisocyanates include oligomeric polyisocyanates including, but not limited to, dimers, such as the uretdione of 1,6-hexamethylene diisocyanate, trimers, such as the biuret, allophonate, and/or isocyanurate of 1,6-hexanediisocyanate and the isocyanurate of isophorone diisocyanate, and polymeric oligomers. Modified polyisocyanates can also be used, including, but not limited to, carbodiimides and uretdiones, and mixtures thereof. In some implementations, however, the non-aromatic polyisocyanate contains biuret, isocyanurate, allophonate, and/or iminooxadiazinedione structures. Polyisocyanates containing iminooxadiazinedione groups, and their preparation, can be found in, for example, EP-A 798 299, EP-A 896 009, EP-A 962 454 and EP-A 962 455. In some implementations, the non-aromatic polyisocyanate comprises aliphatic, aliphatic/cycloaliphatic and/or cycloaliphatic single-type or mixed trimers based on 1,6-diisocyanatohexane ("HDI") and/or isophorone diisocyanate, which are obtainable in accordance, for example, with U.S. Pat. Nos. 4,324,879, 4,288,586, DE-A 310 026 2, DE-A 310 026 3, DE-A 303 386 0 or DE-A 314 467 2, which are incorporated herein by reference. Suitable non-aromatic polyisocyanates are commercially available under the designation DESMODUR® from Covestro LLC, Pittsburgh, Pa. including DESMODUR® N 100 (HDI biuret), DESMODUR® N 3200 (HDI biuret), DESMODUR® N 3300A (HDI trimer), DESMODUR® N 3400 (HDI uretdione), DESMODUR® N 3500 (HDI allophanate trimer, NCO group content of 19.5% by weight, average NCO functionality of 4.6), DESMODUR® N 3900 (Aliphatic polyisocyanate resin based on HDI, NCO group content of 23.5% by weight, average NCO functionality of 3.2), DESMODUR® XP 2617 (largely linear NCO prepolymer based on HDI, NCO group content of 12.5% by weight, average NCO functionality of 2.0), and DESMODUR® XP 2580 (aliphatic polyisocyanate based on HDI, NCO group content of 19.5% by weight, average NCO functionality of 2.5).

In certain implementations, the isocyanate-reactive component and the isocyanate-functional component are present in the coating composition in amounts such that the molar ratio of the isocyanate-reactive groups to isocyanate groups in the coating composition is within the range of 1.0:0.8 to 1.0:2.0.

The coating compositions and foam compositions can optionally include additional additives, as are known in the art, non-limiting examples of which are plasticizers, defoamers, moisture scavengers, thickeners, catalysts, fillers, emulsifiers, surface-active stabilizers, pigments, dyes, UV-stabilizers, hindered-amine light stabilizers, antioxidants, leveling additives, dispersing and grinding aids, impact modifiers, flame-retardants, biocides, and the like. In certain implementations, these additional additives are present in the isocyanate-reactive component prior to its mixture with the isocyanate-reactive component.

Various aspects of the subject matter described herein are set out in the following numbered clauses:

Clause 1. A process for producing a polycyclic polyether polyol having a hydroxyl functionality of 1.5 to 6 and a number average molecular weight of 200 to 12,000 Da, comprising alkoxylating a polyol starter comprising predominantly a polycyclic polyol with an alkylene oxide in the presence of a DMC catalyst.

Clause 2. The process of clause 1, wherein the polycyclic polyether polyol has an arithmetically calculated functionality of 1.5 to 4, 1.5 to 3, 2 to 3, or 2 to 2.5.

Clause 3. The process of clause 1 or clause 2, wherein the polycyclic polyether polyol has a number average molecular weight of 200 Da to 1,500 Da, 200 Da to 1,000 Da, 200 Da to 800 Da, 200 Da to 600 Da, 200 Da to 400 Da, or 250 Da to 350 Da.

Clause 4. The process of one of clause 1 to clause 3, wherein the polycyclic polyether polyol has a viscosity at 25° C. of no more than 7500 cks, no more than 5000 cks, no more than 1500 cks, no more than 1000 cks, or 300 cks to 1,500 cks.

Clause 5. The process of one of clause 1 to clause 4, wherein the polycyclic polyether polyol exhibits an APHA (Pt/Co) color (ASTM D1209-05) of no more than 500, no more than 400, no more than 300, no more than 200, no more than 150, or, in some cases, no more than 100.

Clause 6. The process of one of clause 1 to clause 5, wherein the polycyclic polyol starter comprises a polycyclic diol or a polycyclic triol.

Clause 7. The process of one of clause 1 to clause 6, wherein the polycyclic polyol starter comprises a bicyclic polyol or a tricyclic polyol.

Clause 8. The process of one of clause 1 to clause 7, wherein the rings of the polycyclic group of the polycyclic polyol starter are saturated, i.e., aliphatic.

Clause 9. The process of one of clause 1 to clause 8, wherein the polycyclic groups of the polycyclic polyol starter have a ring size of 3 atoms, 4 atoms, 5 atoms, 6 atoms, and/or 7 atoms.

Clause 10. The process of one of clause 1 to clause 9, wherein the polycyclic groups of the polycyclic polyol starter are unsubstituted or substituted with one or more heteroatoms selected from nitrogen, oxygen, silicon, and/or sulfur.

Clause 11. The process of one of clause 1 to clause 10, wherein the polycyclic polyol starter comprises a dicyclic diol in which the cyclic groups include an ether linkage.

Clause 12. The process of one of clause 1 to clause 11, wherein the polycyclic polyol starter comprises a tricyclodecane unit, a bicyclodecane unit, a norbornane unit, a bicyclooctane unit, a bicyclononane unit, an isosorbide unit, or a bicycloundecane unit.

Clause 13. The process of one of clause 1 to clause 12, wherein the polycyclic polyol starter comprises a 1,4:3,6-dianhydrohexitol, such as isosorbide, isomannide, isoidide, isogalactide, isofucide and isoinoside.

Clause 14. The process of one of clause 1 to clause 13, wherein the polycyclic polyol starter has a purity of greater than 98%, at least 98.5%, at least 99%, or greater than 99.5%.

Clause 15. The process of one of clause 1 to clause 14, wherein the DMC catalyst is used in an amount of at least 0.01% by weight, or at least 0.02% by weight, based on the total weight of the polycyclic polyether polyol.

Clause 16. The process of one of clause 1 to clause 15, wherein the polyol starter further comprises one or more additional hydroxyl and/or amine functional starters comprising trimethylolethane, trimethylolpropane, glycerol, pentaerythritol, 4,4'-dihydroxydiphenyl-propane, sorbitol, sucrose, ethylenediamine, monoethanolamine, diethanolamine, methyl amine, ethylene diamine, diethylene triamine, triethylene tetramine, triethanolamine, ethylene glycol, 1,2- or 1,3-propanediol, 1,2-, 1,3- or 1,4-butanediol, 1,5-heptanediol, 1,6-hexanediol, 1,4-cyclohexanedimethanol, 1,4-cyclohexanedimethanol, 1,3-cyclohexanedimethanol, 1,2-cyclohexanedimethanol, tricyclodecanedimethanol, adamantanediol, pentacyclopentadecanedimethanol, glycerin, pentaerythritol, 4,4'-dihydroxy-diphenylpropane, aniline, 4,4'-methylene dianiline, 2,3-toluene diamine, 3,4-toluene diamine, 2,4-toluene diamine, and 2,6-toluene diamine, ammonia, ethanolamine, triethanolamine, and/or ethylene diamine.

Clause 17. The process of one of clause 1 to clause 16, wherein the polycyclic polyol starter is present in an amount of more than 50% by weight, at least 80% by weight, at least 90% by weight, at least 98% by weight or at least 99% by weight, based on the total weight of H-functional initiator used to prepare the polycyclic polyether polyol.

Clause 18. The process of one of clause 1 to clause 17, wherein the alkylene oxide comprises ethylene oxide, propylene oxide, butylene oxide, styrene oxide, epichlorohydrin, or a mixture of any two or more thereof.

Clause 19. The process of one of clause 1 to clause 18, wherein the DMC catalyse comprises zinc hexacyanocobaltate(II), zinc hexacyano-ferrate(III), nickel hexacyanoferrate (II), or cobalt hexacyano-cobaltate(III).

Clause 20. A process for producing a polycyclic polyether polyol having a hydroxyl functionality of 1.5 to 3 and a number average molecular weight of 200 to 800 Da, comprising alkoxylating a polyol starter consisting essentially of a 1,4:3,6-dianhydrohexitol having a purity of greater than 98%, with an alkylene oxide in the presence of a DMC catalyst, wherein the DMC catalyst is used in an amount of at least 0.01% by weight or 0.02% by weight, based on the total weight of the polycyclic polyether polyol.

Clause 21. The process of clause 20, wherein the polycyclic polyether polyol has an arithmetically calculated functionality of 2 to 3, or 2 to 2.5.

Clause 22. The process of clause 20 or clause 21, wherein the polycyclic polyether polyol has a number average molecular weight of 200 Da to 600 Da, 200 Da to 400 Da, or 250 Da to 350 Da.

Clause 23. The process of one of clause 20 to clause 22, wherein the polycyclic polyether polyol has a viscosity at 25° C. of no more than 7500 cks, no more than 5000 cks, no more than 1500 cks, no more than 1000 cks, or 300 cks to 1,500 cks.

Clause 24. The process of one of clause 20 to clause 23, wherein the polycyclic polyether polyol exhibits an APHA (Pt/Co) color (ASTM D1209-05) of no more 500, no more than 400, no more than 300, no more than 200, no more than 150, in some cases, no more than 100.

Clause 25. The process of one of clause 20 to clause 24, wherein the 1,4:3,6-dianhydrohexitol has a purity of at least 98.5%, at least 99%, or greater than 99.5%.

Clause 26. The process of one of clause 20 to clause 25, wherein the polyol starter further comprises one or more additional hydroxyl and/or amine functional starters comprising trimethylolethane, trimethylolpropane, glycerol, pentaerythritol, 4,4'-dihydroxydiphenyl-propane, sorbitol, sucrose, ethylenediamine, monoethanolamine, diethanolamine, methyl amine, ethylene diamine, diethylene triamine, triethylene tetramine, triethanolamine, ethylene glycol, 1,2- or 1,3-propanediol, 1,2-, 1,3- or 1,4-butanediol, 1,5-heptanediol, 1,6-hexanediol, 1,4-cyclohexanedimethanol, 1,4-cyclohexanedimethanol, 1,3-cyclohexanedimethanol, 1,2-cyclohexanedimethanol, tricyclodecanedimethanol, adamantanediol, pentacyclopentadecanedimethanol, glycerin, pentaerythritol, 4,4'-dihydroxy-diphenylpropane, aniline, 4,4'-methylene dianiline, 2,3-toluene diamine, 3,4-toluene diamine, 2,4-toluene diamine, and 2,6-toluene diamine, ammonia, ethanolamine, triethanolamine, and/or ethylene diamine.

Clause 27. The process of one of clause 20 to clause 26, wherein the 1,4:3,6-dianhydrohexitol is present in an amount of at least 98% by weight or at least 99% by weight, based on the total weight of H-functional initiator used to prepare the polycyclic polyether polyol.

Clause 28. The process of one of clause 20 to clause 27, wherein the alkylene oxide comprises ethylene oxide, propylene oxide, butylene oxide, styrene oxide, epichlorohydrin, or a mixture of any two or more thereof.

Clause 29. The process of one of clause 20 to clause 28, wherein the DMC catalyse comprises zinc hexacyanocobaltate(II), zinc hexacyano-ferrate(III), nickel hexacyanoferrate(II), or cobalt hexacyano-cobaltate(III).

Examples

Various polyether polyols were prepared in a stainless steel stirred reactor using the ingredients listed in Table 1 using the following procedure. To the reactor, the starter and alkoxylation catalyst were charged at ambient temperature, except that, when using isosorbide, the starter was melted in an oven at 80° C. before being charged to the reactor in liquid form. When using BHMTD and isosorbide (in Polyol Examples 17 & 18), the starter was charged in its solid form. In some instances, a small amount of a suitable organic acid was added to neutralize any residual alkalinity contained in the starter. The reactor temperature was raised to the desired temperature at which point the mixture was de-watered using vacuum distillation with a slight nitrogen sparge through the mixture. The reactor was then sealed under vacuum and a small amount (i.e. 8% by weight based on the amount of starter) of alkylene oxide was added to initiate the alkoxylation catalyst, if needed. Based on the drop in reactor pressure, this initiation amount of alkylene oxide may be repeated. In the case of the high purity polycyclic polyol starter, it was discovered that the catalyst did not become fully active until the calculated molecular weight of the polycyclic polyether polyol was 220 Da. Once the alkoxylation catalyst was fully active (as determined by a drop in reactor pressure), the desired amount of alkylene oxide was continuously added to the reactor at a rate sufficient to maintain the reaction pressure (typically below 55 psig). Once the desired amount of alkylene oxide was fed, the reactor was held at the reaction temperature for a sufficient time to fully react any unreacted oxide. The reaction mixture was stripped using vacuum distillation with a slight nitrogen sparge through the mixture. The reactor was cooled to ~90° C. and the reactor was charged with 500 ppm of Irganox® 1076 antioxidant and agitated for 30 minutes before the final polyol was collected. When potassium hydroxide was used as the alkoxylation catalyst, the catalyst was removed by neutralizing with a suitable organic acid and the resultant salts were filtered from the final polyol. When DMC was used as the alkoxylation catalyst, no catalyst removal step was necessary. Results are set forth in Table 1.

TABLE 1

| | Example | | | | | |
|---|---|---|---|---|---|---|
| | 1 | 2 | 3 | 4 | 5 | 6 |
| Target Polyol MW | 300 Da | 300 Da | 300 Da | 300 Da | 1000 Da | 2000 Da |
| Starter | Isosorbide[1] | Isosorbide[2] | Isosorbide[2] | BHMTD[5] | Polyol Example 4 | Polyol Example 5 |
| wt (gms) | 326.5 | 314.5 | 317.6 | 398.2 | 196.2 | 301.0 |
| Phosphoric Acid[3] (ppm) | None | None | 429 | 211 | None | None |
| Catalyst | DMC[4] | DMC[4] | DMC[4] | DMC[4] | DMC[4] | DMC[4] |
| ppm (final) | 304.3 | 381.7 | 307.1 | 200.4 | 199.1 | 201.1 |
| wt (gms) | 0.1313 | 0.1299 | 0.1298 | 0.1237 | 0.0909 | 0.0594 |
| PO Feed temp (° C.) | 110-120-130 | 120-130 | 110-120-130 | 130 | 130 | 130 |
| wt (gms) | 104.9 | 25.7 | 104.9 | 218.7 | 457.6 | 292.1 |
| Mole PO/Mole Starter | 0.81 | 0.21 | 0.83 | 1.86 | 14.44 | 32.47 |
| Appearance | N/A[a] | N/A[a] | N/A[a] | Clear | Clear | Clear |
| OH# (mg KOH/gm) | — | — | — | 358 | 104 | 53.2 |
| Viscosity (cks @ 25° C.) | — | — | — | 5079 | 443 | 577 |
| Acid (mg KOH/gm) | — | — | — | 0.009 | 0.006 | 0.006 |
| Color (Plat Co) | — | — | — | 33.5 | 25.7 | 36.3 |
| Water (%) | — | — | — | 0.010 | 0.013 | 0.011 |

| | Example | | | | | |
|---|---|---|---|---|---|---|
| | 7 | 8 | 9 | 10 | 11 | 12 |
| Target Polyol MW | 300 Da | 1000 Da | 2000 Da | 500 Da | 300 Da | 500 Da |

TABLE 1-continued

| Starter | Isosorbide[2] | Polyol Example 7 | Polyol Example 8 | Isosorbide[2] | Isosorbide[1] | Isosorbide[2] |
|---|---|---|---|---|---|---|
| wt (gms) | 312.9 | 198.2 | 300.5 | 194.3 | 195.7 | 197.0 |
| Phosphoric Acid[3] (ppm) | 237 | None | None | None | 315 | None |
| Catalyst | DMC[4] | DMC[4] | DMC[4] | DMC[4] | DMC[4] | DMC[4] |
| ppm (final) | 499.3 | 199.1 | 198.7 | 498.2 | 771.0 | 395.1 |
| wt (gms) | 0.3250 | 0.0318 | 0.0590 | 0.3252 | 0.3260 | 0.2616 |
| PO Feed temp (° C.) | 130 | 130 | 130 | 130 | 130 | 130 |
| wt (gms) | 337.4 | 458.3 | 297.2 | 457.8 | 226.6 | 464.6 |
| Mole PO/Mole Starter | 2.77 | 15.11 | 32.80 | 6.04 | 2.91 | 6.05 |
| Appearance | Clear | Clear | Clear | Clear | Clear | Clear |
| OH# (mg KOH/gm) | 362 | 108 | 54.2 | 223 | 341 | 226 |
| Viscosity (cks @ 25° C.) | 1335 | 382 | 537 | 507 | 1203 | 505 |
| Acid (mg KOH/gm) | 0.017 | 0.005 | 0.003 | 0.004 | 0.020 | <0.001 |
| Color (Plat Co) | 74.3 | 37.3 | 36.6 | 144 | 16.9 (Gardner) | 121.4 |
| Water (%) | 0.012 | 0.011 | 0.009 | 0.020 | 0.116 | 0.033 |

| | Example | | | | | |
|---|---|---|---|---|---|---|
| | 13 | 14 | 15 | 16 | 17 | 18 |
| Target Polyol MW | 500 Da | 500 Da | 500 Da | 300 Da | 300 Da | 300 Da |
| Starter #1 | Isosorbide[2] | Isosorbide[2] | Isosorbide[5] | Isosorbide[5] | Isosorbide[1] | Isosorbide[2] |
| wt (gms) | 200.5 | 160.5 | 193.1 | 323.0 | 1988.9 | 2002.3 |
| Starter #2 | — | Polyol Example 12 | — | — | — | — |
| wt (gms) | — | 97.3 | — | — | — | — |
| Phosphoric Acid[3] (ppm) | None | None | 276 | 235 | None | None |
| Catalyst | DMC[4] | DMC[4] | DMC[4] | DMC[4] | KOH[7] | KOH[7] |
| ppm (final) | 287.9 | 410.2 | 302.3 | 296.3 | 3080 | 4090 |
| wt (gms) | 0.1953 | 0.2333 | 0.1965 | 0.1950 | 27.72 | 37.10 |
| PO Feed temp (° C.) | 130 | 130 | 130 | 130 | 110 | 110 |
| wt (gms) | 477.4 | 378.7 | 456.5 | 334.7 | 2090.9 | 2101.5 |
| Mole PO/Mole Starter | 6.11 | 5.12 | 6.07 | 2.66 | 2.65 | 2.69 |
| Appearance | Clear | Clear | Clear | Clear | Clear | Clear |
| OH# (mg KOH/gm) | 226 | 215 | 223 | 377 | 405 | 364 |
| Viscosity (cks @ 25° C.) | 508 | 507 | 517 | 1502 | 1154 | 880 |
| Acid (mg KOH/gm) | <0.001 | 0.011 | 0.016 | 0.016 | 0.267 | 0.177 |
| Color (Plat Co) | 175.2 | 115.7 | 236.7 | 450.9 | >500 | 523.2 |
| Water (%) | 0.034 | 0.029 | 0.043 | 0.024 | 0.033 | 0.011 |

[a]Reaction was terminated before catalyst was fully activated
[1]98% purity isorsorbide commercially available from Acros Organics.
[2]>99.5% purity isosorbide commercially available from Roquette Frères as Polysorb P.
[3]85% aqueous phosphoric acid commercially available from Sigma Aldrich.
[4]substantially amorphous zinc hexacyanocobaltate t-butyl alcohol complex catalysts.
[5]4,8-Bis(hydroxymethyl) tricyclo[5.2.1.0$^{2,6}$] decane commercially available from Sigma Aldrich.
[6]98% purity isosorbide (pellet form) commercially available from Roquette Frères as Polysorb PBA.
[7]45% aqueous potassium hydroxide commercially available from Fisher Scientific.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a polycyclic polyether polyol having a hydroxyl functionality of 1.5 to 6 and a number average molecular weight of 200 to 12,000 Da, comprising alkoxylating a polyol starter comprising predominantly a polycyclic polyol with an alkylene oxide in the presence of a DMC catalyst.

2. The process of claim 1, wherein the polycyclic polyether polyol has a functionality of 2 to 3.

3. The process of claim 2, wherein the polycyclic polyether polyol has a number average molecular weight of 200 Da to 600 Da.

4. The process of claim 3, wherein the polycyclic polyether polyol has a viscosity at 25° C. of no more than 7500 cks.

5. The process of claim 3, wherein the polycyclic polyether polyol exhibits an APHA color of no more than 500.

6. The process of claim 1, wherein the polycyclic polyol starter comprises a polycyclic diol.

7. The process of claim 6, wherein the polycyclic diol starter comprises a bicyclic diol.

8. The process of claim 7, wherein the bicyclic diol starter includes an ether linkage.

9. The process of claim 1, wherein the polycyclic polyol starter comprises a tricyclodecane unit, a bicyclodecane unit, a norbornane unit, a bicyclooctane unit, a bicyclononane unit, an isosorbide unit, or a bicycloundecane unit.

10. The process of claim 1, wherein the polycyclic polyol starter comprises a 1,4:3,6-dianhydrohexitol.

11. The process of claim 10, wherein the 1,4:3,6-dianhydrohexitol starter is used in an amount of at least 90% by weight, based on the total weight of starter.

12. The process of claim 10, wherein the 1,4:3,6-dianhydrohexitol starter has a purity of greater than 98%.

13. The process of claim 12, wherein the purity of the 1,4:3,6-dianhydrohexitol starter is at least 98.5%.

14. The process of claim 13, wherein the DMC catalyst is present in an amount of at least 0.01% by weight, based on the total weight of the polycyclic polyether polyol.

15. The process of claim 1, wherein the polycyclic polyol starter is present in an amount of at least 80% by weight, based on the total weight of starter.

16. The process of claim 1, wherein the polycyclic polyol starter comprises a polycyclic polyether polyol.

17. A process for producing a polycyclic polyether polyol having a hydroxyl functionality of 1.5 to 3 and a number average molecular weight of 200 to 800 Da, comprising alkoxylating a polyol starter consisting essentially of a 1,4:3,6-dianhydrohexitol having a purity of greater than 98%, with an alkylene oxide in the presence of a DMC catalyst.

18. The process of claim 17, wherein the polycyclic polyether polyol has a functionality of 2 to 3.

19. The process of claim 18, wherein the polycyclic polyether polyol has a number average molecular weight of 200 Da to 600 Da.

20. The process of claim 17, wherein the purity of the 1,4:3,6-dianhydrohexitol is at least 98.5%.

21. The process of claim 17, wherein the polyol starter further comprises a polycyclic polyether polyol.

* * * * *